United States Patent [19]

Slavetskas

[11] 4,437,459
[45] Mar. 20, 1984

[54] HEMI-SLING

[76] Inventor: Deborah Slavetskas, 5 Laine Ct., Appalachin, N.Y. 13732

[21] Appl. No.: 428,181

[22] Filed: Sep. 29, 1982

[51] Int. Cl.$^3$ .......................... A61F 5/40; A61F 13/00
[52] U.S. Cl. ...................................... 128/94; 128/133; 128/DIG. 15
[58] Field of Search .................. 128/94, 133, DIG. 15

[56] References Cited

U.S. PATENT DOCUMENTS

| 1,304,153 | 5/1919 | Bugge | 128/94 |
| 1,808,422 | 6/1931 | MacDonald | 128/94 |
| 1,991,677 | 2/1935 | Jacks | 128/94 |
| 2,460,589 | 2/1949 | Lewis | 128/94 |
| 3,215,138 | 11/1965 | Groesbeck | 128/94 |
| 3,815,588 | 6/1974 | Klausner | 128/94 |
| 4,071,022 | 1/1978 | Ewers | 128/94 |
| 4,188,944 | 2/1980 | Augustyniak | 128/94 |
| 4,220,149 | 9/1980 | Mims, Jr. | 128/94 |
| 4,285,337 | 8/1981 | Cosentino | 128/94 |
| 4,355,635 | 10/1982 | Bihl et al. | 128/94 |

Primary Examiner—John D. Yasko
Assistant Examiner—C. W. Shedd
Attorney, Agent, or Firm—Michael F. Brown

[57] ABSTRACT

A sling, especially for hemiplegics, having supports for hand and elbow made of flexible material. The elbow support is suspended from two straps, one over each shoulder, holding the affected shoulder in place and preventing subluxation of the joint. The hand support is suspended adjustably from a third strap attached at mid-chest to one of the others, and supports the hand in a natural, functional, supinated position.

9 Claims, 3 Drawing Figures

HEMI-SLING

BACKGROUND OF THE INVENTION

The invention pertains to slings for supporting the arms or patients, especially those who have suffered injury or disability, possibly caused by a stroke, which has resulted in paralysis of one side (hemiplegia).

Paralysis of one side, or hemiplegia, causes a number of problems related to the arm of the patient. The lack of muscle control can lead to separation of the shoulder joint (subluxation) if the arm is not properly supported. Swelling (edema) results in those lower parts of the limb, especially the hand and fingers, in which the blood tends to pool. The shoulder may "roll in" or turn forward (protraction).

Prior art slings intended for sprains or fractures do not prevent any of these problems. (see, e.g. U.S. Pat. Nos. 3,730,164 to Rash, or 2,539,677 to Teale). Those slings most commonly supplied to stroke victims are heavy, uncomfortable, and difficult to put on. They tend to restrict the movement of the affected limb to a great extent, leading to discomfort and difficulty in balance. The hand is allowed to droop in a palm-down position (pronation). This is unnatural and leads to edema in the fingers, and to other ill effects due to pinching of nerves and blood vessels.

U.S. Pat. No. 4,214,579 issued in 1980 to Ford, shows one such prior-art sling, and is illustrative of the problems common to most such appliances. The arm is supported by a rigid plastic holder, which adds to the complexity, expense, weight and discomfort of the sling. Common to many such devices, the support strap passes directly over the patient's shoulder to the hand. This can be extremely uncomfortable for women, with one breast compressed by the strap. The complexity makes the design difficult for stroke victims to put on without aid. The constant pressure of the rigid support can lead to discomfort and sores. Ford makes an attempt to avoid the pronation present in earlier designs (see, e.g. Sanders U.S. Pat. No. 2,594,809), at the cost of additional complexity and custom molding. The shoulder is not well protected from subluxation. Lausner, U.S. Pat. No. 3,815,588, shows another example of this rigid-type sling, having much the same drawbacks as Ford.

SUMMARY OF THE INVENTION

The invention presents a sling, expecially suitable for use with hemiplegics, which is light, comfortable and inexpensive to produce. The patient's hand is supported in a soft, flexible, holder in a palm-up (supinated) position, which is natural and functional. The elbow is supported by two straps, one over each shoulder, which supports the affected arm to prevent subluxation and protraction, while allowing a degree of freedom of movement not present in earlier designs. The hand support is adjustably suspended from one of these straps, which allows the straps to pass around, rather than over, the patients breasts, at a major improvement in comfort for female patients. The separable hand support makes the sling vastly easier for stroke victims to put on, while allowing for a variety of positions of the forearm. The hand support may be detached without loss of shoulder support, another feature lacking in earlier designs.

DESCRIPTION OF THE PREFERRED EMBODIMENT

Figure 1:
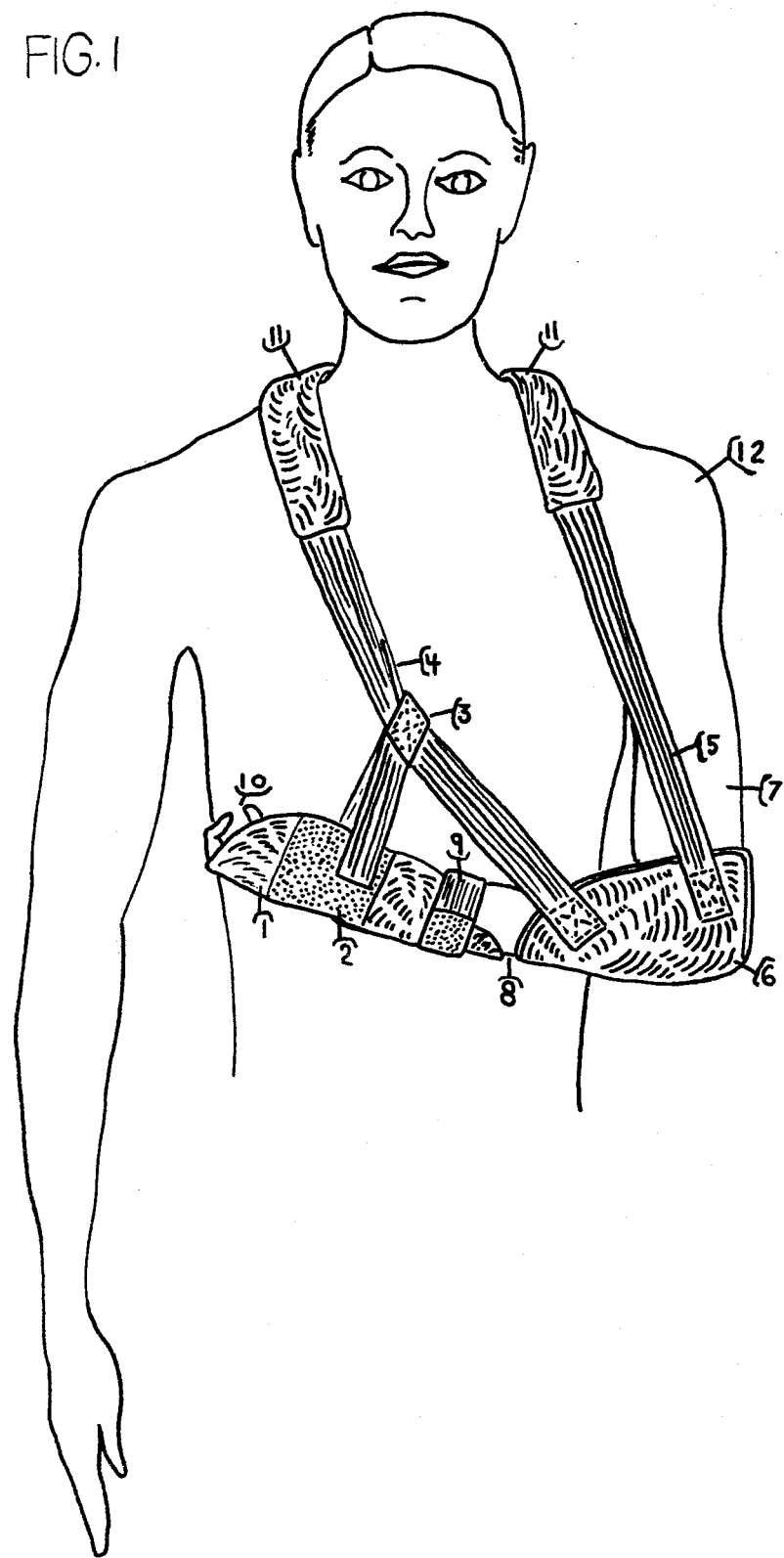
FIGS. 1 and 2 show a front and rear view, respecitvely, of a patient wearing the preferred embodiment of the invention.
Figure 2:
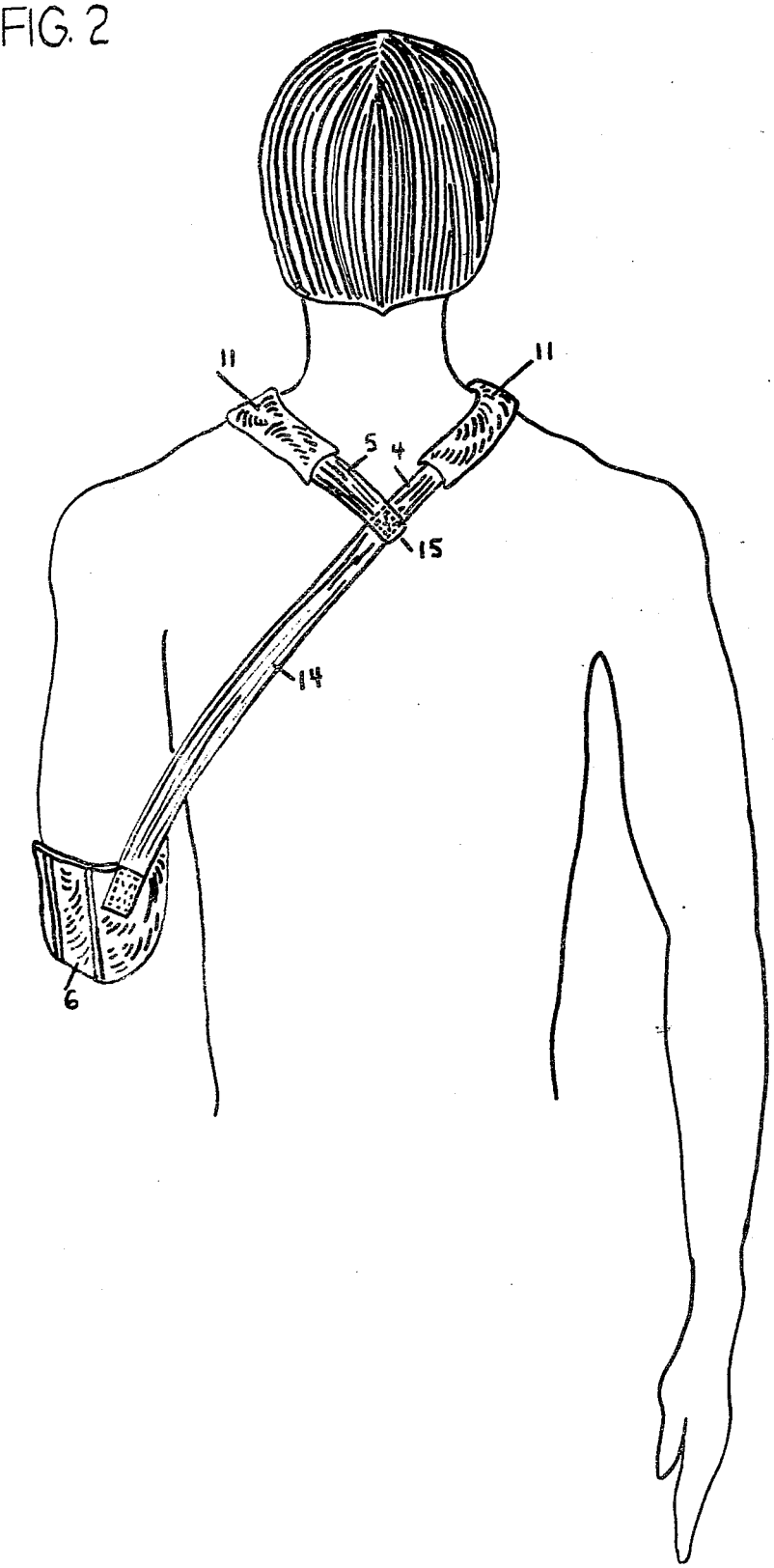

Referring to FIGS. 1 and 2, the preferred embodiment of the invention comprises supporting elements for the hand (1) and elbow (6) of the patient, connected and supported by three straps (3), (4) and (5).

The support elements (1) and (6) are constructed of a light, flexible material for comfort, lack of weight and freedom from the ill effects of pressure by a rigid member. A durable cloth material, preferably a denim, is ideal for these elements. The cloth may be doubled, with padding in between the layers, for added comfort. The cloth may be easily washed, an added advantage.

The elbow support (6) is large enough to encompass the patients' elbow and parts of the forearm (8) and upper arm (7), holding the elbow firmly but comfortably. Attached to the elbow support (6) is a main strap (4) which crosses the center of the patients' chest, and over the opposite shoulder, crossing the patients' back, approximately at the shoulder blades, and attaches back to the elbow support. A second strap (5), also attached to the elbow support, crosses the other shoulder and joins the first strap (4) at a point (15) between the shoulder blades. A third strap (3), intended to support the hand, is attached by its midpoint to the first strap at a point in mid-chest. This combination of straps supports the upper arm (7) in the shoulder joint (12) to prevent separation (subluxation). Neither strap presses on the wearer's breasts, avoiding a major source of discomfort. Preferably, shoulder pads (11) are provided where the straps, (4) and (5), cross the patients' shoulders.

Figure 3:
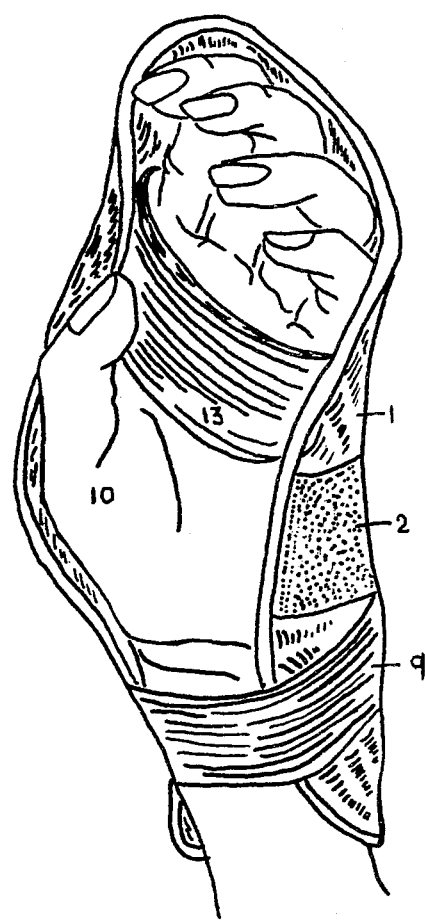
FIG. 3 shows a detail of the preferred embodiment of the hand support.

The hand support (1) supports the patients' hand (10) in a supinated (palm-up) position in a pouch of material. It is attached to the ends of the third strap (3) by a fastening means, which is preferably of the Velcro TM type (2). Alternatively, a plurality of buttons or hooks could be provided. Referring to FIG. 3, the support (1) is secured to the hand (10) by a wrist strap (9) and palm strap (13). The wrist strap (9) may be a soft elastic material or, preferably, a strap with Velcro TM fastener. The palm strap (13) is preferably of soft elastic material. In the preferred embodiment, a removable pad (not shown) is provided in the hand support for added comfort and improved washability.

It should be noted that, while the invention has been described here as especially adapted to the special problems of Hemiplegics, the sling is also useful for other problems involving the arm or shoulder. These include sprains, dislocations, and fractures of the Humerus (upper arm), elbow, radius, ulna, wrist or hand.

It is to be understood that the embodiment of the invention herein described is merely illustrative of the application of the principles of the invention. Reference herein to details of the illustrated embodiments are not intended to limit the scope of the claims which themselves recite those features regarded as essential to the invention.

I claim:

1. A sling for supporting the hand, shoulder, elbow and upper and lower arm of a patient comprising:

(a) elbow containing means for enclosing the elbow of the arm to be supported, made of flexible material;

(b) first strap means having first and second ends and a flexible middle portion therebetween, attached at both ends to the elbow containing means;

(c) second strap means, having first and second ends and a flexible middle portion therebetween, attached at the first end to the elbow containing means;

(d) third strap means, having two ends and a flexible middle portion therebetween, the middle portion being attached to the middle portion of the first strap means at a point along the length of the middle portion of the first strap means, the point of attachment being chosen to fall in mid-chest of the patient;

(e) The length of the first strap means being chosen such that the first strap means can comfortably pass from its first end at the elbow containing means with the patient's elbow therein, across approximately the middle of the patient's chest, around the patient's neck and shoulder on the side opposite the arm to be supported, and down across the patient's shoulder blades and back to the second end at the elbow containing means;

(f) The second end of the second strap means attaching to the middle portion of the first strap means at a point located on the center line of the patient's back;

(g) The length of the second strap means being chosen such that the second strap means passes from the elbow supporting means over the patient's shoulder to the first strap means, and the patient's arm is supported by the elbow containing means, holding the upper arm in a natural position without strain on the shoulder joint;

(h) hand supporting means comprising: a body adapted to enclosing the back of the patient's hand made of flexible material, adjustable wrist strap means for securing the body at one end to the patient's wrist, palm strap means for securing the body to the patient's hand, crossing the palm of the hand across the base of the fingers; and fastening means for attaching the body to the ends of the third strap means;

(i) the ends of the third strap means being adapted to adjustably mate with the fastening means of the hand supporting means, whereby the patient's hand is supported in a natural functional position in supination, with the hand in an adjustable position higher than the elbow.

2. The sling of claim 1 further comprising pad means for cushioning the first strap means, attached to the middle portion of the first strap means at least at the point where the first strap means crosses the patient's shoulder and neck, whereby the first strap is cushioned at the point of greatest pressure on the patient.

3. The sling of claim 1 further comprising pad means for cushioning the second strap means, attached to the middle portion of the second strap means at least at the point where the second strap means crosses the patient's shoulder, whereby the second strap is cushioned at the point of greatest pressure on the patient.

4. The sling of claim 1 in which the hand supporting means further comprises soft, washable padding means for cushioning the back of the patient's hand at its point of contact with the hand supporting means.

5. The sling of claim 4 in which the padding means is removable for cleaning.

6. The slings of claim 1 in which the flexible material of the elbow containing means and the hand supporting means is durable cloth.

7. The sling of claim 6 in which the cloth is denim.

8. The sling of claim 1 in which the fastening means of the hand supporting means is cohesive hooked and plush material.

9. The sling of claim 1 in which the palm strap means of the hand supporting means is elastic.

* * * * *